Oct. 18, 1960 F. C. HART Plant Pat. 1,977
AZALEA PLANT
Filed Nov. 24, 1959
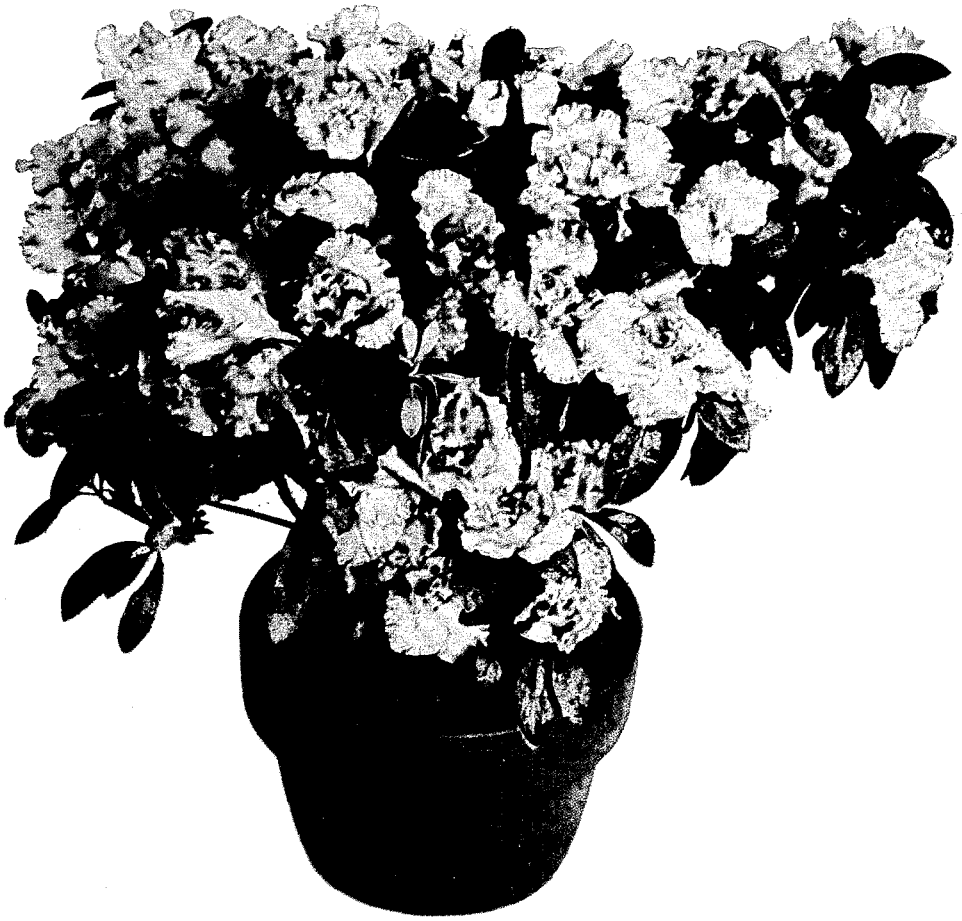
Fred C. Hart
INVENTOR
BY Ramsey and Kolisch
Attys.

United States Patent Office

Plant Pat. 1,977
Patented Oct. 18, 1960

1,977

AZALEA PLANT

Fred C. Hart, Rte. 3, Box 207, Mount Vernon, Wash.

Filed Nov. 24, 1959, Ser. No. 855,249

1 Claim. (Cl. 47—60)

The present invention relates to a new and distinct variety of azalea plant which was originated by me by crossing two unnamed and unpatented varieties. The original seedling was observed in a flat containing over 100 seedlings and the majority of said seedlings followed the general coloration of Paul Schame (unpatented).

As a result of this crossing I have produced a new variety of azalea plant which is distinguished from Paul Schame as well as from other varieties of its class of which I am aware, in the following combination of characteristics which are outstanding in the new variety:

(1) It is characterized by a bloom of large diameter which the form of the flower might be likened to the gardenia;

(2) The flowers and the petals thereof are characterized by a deeply ruffled peripheral margin and are of greater thickness and have a leathery texture which is not found in Paul Schame. It is a double Indica (Belgium), and the petals hold tenaciously over a blooming season of approximately four to six weeks in length. In this regard it differs from the seed parent Paul Schame both in keeping qualities and in its deep ruffling.

(3) When buds initially form, they are substantially longer and larger in diameter than buds formed upon the seed parent Paul Schame;

(4) The new variety of azalea produces a flower which is highly crowned and those petals lying inwardly of the marginal petals stand more erect than do the petals in Paul Schame. They also appear as primary petals rather than secondary petals not only in size but also in their tendency to stand upright.

The color of the flowers of my new variety resemble closely those of Paul Schame but in size they are approximately 50% larger in diameter and approximately twice as heavy due to the greater fullness and heavier texture thereof.

The unique combinations of the characteristics of my new variety as noted above makes the same a valuable and desirable type of hybrid azalea for commercial use for the reason that the flowers may be brought in early or late in the growing season to suit the market. This is particularly true because this species may be forced for the Christmas trade. It is a profuse grower.

Asexual reproduction of my new variety by cuttings at Mt. Vernon, Washington, shows the foregoing characteristics and distinctions come true to form and coloration, are established, and are transmitted through succeeding propagations.

The accompanying photographic reproduction shows a typical specimen plant of my new variety depicted in color, with the flowers thereof being substantially mature, the colors being shown as nearly true as is reasonably possible in a color illustration of this character.

The following is a detailed description of my new variety as based upon observations made in Mt. Vernon, Washington, with color terminology in accordance with Robert F. Wilson's Horticultural Colour Chart, as issued by the British Color Council in collaboration with the Royal Horticultural Society, except where general color terms of ordinary dictionary significance are obvious:

Type: Evergreen.
Parentage: Seedling.
*Seed parent.*—An unknown azalea but resembling and probably Paul Schame.
*Pollen parent.*—An unnamed and unknown azalea.

*Plant*

Form of plant: Bush; branches strong and woody.
Growth habit: Compact and free.
Rooting: Roots easily.
Blooming habit: Free, large, profuse blooms.
Blooming season: Can readily be forced to bloom from December through May in plants grown in Mt. Vernon, Washington.
Foliage:
*Size.*—Large, two to two and one-half inches in length.
*Quantity.*—Abundant.
*Shape.*—Ovate.
*Texture.*—Top face glossy, Plate 0960 Spinach Green; under face roughened, similar to Paul Schame.
*Edge.*—Smooth.

*Flower*

Flowers borne: 1 to 3 to a bud on strong stems which hold the flowers erect.
Quantity of bloom: Abundant both indoors and in greenhouse.
Continuity: Long growing season. Permanence—four to six weeks resistant to fading in the sun.
Petalage:
*Number of petals under normal conditions.*—Normally ten.
*Color of open flower.*—Porcelain Rose, Plate 620/1. There are slight gradations in color of the petals and although Porcelain Rose is the closest approximation of the observable color, portions of the petals fall within coloration charts carried by page 147 of the Horticultural Color Chart.
*Texture.*—Firm, crisp, leathery.
*Shape.*—Deep, profusely ruffled on the edges and growing to an average diameter of three and one half inches between opposite tips of petals.
*Arrangement.*—Usually in clusters of two flowers which stand firmly erect but vary from one to three flowers in a group.

*Reproductive organs*

Stamens: 4 to 10 per flower. Color—blends from a pale green to a blood red which is darker than the color of the petals.
Pollen: Color—creamy.
Styles: Normal.
Ovaries: Four.

I claim:

A new and distinct variety of azalea plant of evergreen type and of Indica (Belgium) strain substantially as shown and described herein, characterized particularly by large, deeply ruffled double flowers whose petals have a leathery texture and remain tenaciously in place, and delicately roseate with a silvery sheen, which flowers stand erect and hold their color with minimal fading.

No references cited.